United States Patent [19]

Rosencwaig

[11] 4,255,971
[45] Mar. 17, 1981

[54] THERMOACOUSTIC MICROSCOPY

[76] Inventor: Allan Rosencwaig, 134 Timberline Ct., Danville, Calif. 94526

[21] Appl. No.: 956,668

[22] Filed: Nov. 1, 1978

[51] Int. Cl.³ .............................................. G01N 29/04
[52] U.S. Cl. ........................................ 73/606; 73/643
[58] Field of Search ................. 73/606, 607, 608, 618, 73/643, 627; 340/1 R, 3 R, 5 MP, 5 H; 367/7, 8, 13

[56] References Cited

U.S. PATENT DOCUMENTS

| 4,028,933 | 6/1977 | Lemons et al. ........................ 73/627 |
| 4,091,681 | 5/1978 | Hordvik ................................. 73/574 |
| 4,137,991 | 2/1979 | Melcher et al. ....................... 73/643 |

OTHER PUBLICATIONS

Wong et al., "Surface and Subsurface Structure of Solids by Laser Photoacoustic Spectroscopy," Appl. Phys. Lett., B2, (9), pp. 538–539, May 1, 1978.
Kessler, "Review of Progress and Applications in Acoustic Microscopy," J. Acoust. Soc. Am., vol. 55, No. 5, pp. 909–918, May 1974.
White, "Generation of Elastic Waves by Transient Surface Heating," Journal of Applied Physics, vol. 34, No. 12, pp. 3559–3567, Dec. 1963.

Primary Examiner—Stephen A. Kreitman
Attorney, Agent, or Firm—Henry P. Sartorio

[57] ABSTRACT

Method and apparatus for thermoacoustic or thermal wave microscopy to detect surface and subsurface information from a material on a microscopic scale. A thermal wave is generated in a material by causing periodic, localized heating at a microscopic spot by focusing intensity modulated light, or electromagnetic radiation or particle beam, on the spot. The thermoacoustic signal produced provides information about material composition, structure, and the presence of energy deexcitation processes such as fluorescence, photochemistry and photovoltaic processes. The sample is scanned as a two-dimensional array of microscopic spots. Full depth-profiling of the material is provided by varying the modulation frequency of the energy source.

34 Claims, 3 Drawing Figures

THERMOACOUSTIC MICROSCOPY

BACKGROUND OF THE INVENTION

The invention relates to the field of photoacoustics, and more particularly to thermoacoustic or thermal wave microscopy for the microscopic examination of materials, expecially bulk solids, by photoacoustic methods.

The photoacoustic effect was first discovered about one hundred years ago. The photoacoustic effect arises when intensity-modulated light, or other form of electromagnetic radiation, is absorbed by a sample, thereby exciting energy levels within the sample. These levels deexcite generally through a non-radiative or heat-producing process. Thus the absorption of intensity-modulated electromagnetic radiation at any point in the sample results in a periodic localized heating of the sample medium.

The field of photoacoustics has undergone extensive development in the past few years, particularly in the area of photoacoustic spectroscopy. Applicant's prior U.S. patents, U.S. Pat. Nos. 3,948,345 and 4,028,932, disclose a photoacoustic method for spectroscopically analyzing solid substances and a photoacoustic cell. Also see applicant's paper A. Rosencwaig, *Optoacoustic Spectroscopy and Detection*, (Y.H. Pao, ed.), Ch. 8, Academic Press, N.Y., 1977.

Photoacoustic studies on gaseous samples are generally performed using a microphone as a detector. The gaseous sample is contained in an acoustically sealed chamber which also contains a sensitive microphone. Light, chopped or intensity-modulated at a frequency in the range 20-10,000 Hz enters the chamber through a non-absorbing window. If the gas sample absorbs any of the incident photons, energy levels are excited in the gas molecules. When these levels deexcite, some or all of the energy is transferred through collisional processes to kinetic energy of the molecules. The gas thus undergoes a periodic heating as a result of the absorption of the intensity-modulated light, creating thermal waves. This periodic heating in turn results in a periodic pressure rise in the gas, and these pressure fluctuations or acoustic waves are then detected by the microphone.

A great deal of the current work in photoacoustic spectroscopy involves the investigation of non-gaseous materials, such as powders, that are highly light scattering. A similar gas-microphone technique is used. The powder sample is placed in an acoustically sealed cell which also contains a nonabsorbing gas and a sensitive microphone. The incident light is intensity modulated or chopped at a frequency in the range of 20-10,000 Hz. If the powder sample absorbs any incident photons, energy levels in the sample are excited. Deexcitation through non-radiative processes will produce internal heating of the sample. This, in turn, will result in a periodic heat flow or thermal wave from the sample to the surrounding gas. The gas layer near the solid particles undergoes a periodic heating from this heat flow, and this results in an acoustic pressure signal or acoustic wave in the cell that is detected by the microphone. Although indirect, the gas microphone technique is fairly sensitive for measuring the internal heating of a powder sample because of the large surface:volume ratio of the powder.

Photoacoustics of a bulk solid sample are often best measured using the piezoelectric method. The gas-microphone method usually does not work well because of the low surface:volume ratio for the solid and the consequent reduction in heat transfer from the sample to the gas in the cell. The amount of internal heating in the bulk solid is efficiently measured by a piezoelectric transducer in direct contact with the sample. The piezoelectric transducer detects an acoustic wave generated in the solid by the thermal wave produced through the absorption of incident light. A lead zirconate titanate crystal or PZT is a suitable piezoelectric. The sample is illuminated with intensity-modulated light, with modulation frequencies into the megahertz range if desired because of the wide bandwidth response of the piezoelectric detector.

Recently there have been some experiments related to the possibility of performing photoacoustics on a microscopic scale. Von Gutfeld and Melcher, "20-MHz Acoustic Waves From Pulsed Thermo-elastic Expansions of Constrained Surfaces", Appl. Phys. Lett., Vol. 30, No. 6, p. 257, Mar. 15, 1977, describe the generation of acoustic waves in a material by focusing a pulsed laser beam onto the material, and use a piezoelectric detector. However, they operate at a very high frequency of 20 MHz to produce acoustic waves. The surface is constrained to enhance the signal. Wong et al, "Surface and Subsurface Structure of Solids by Laser Photoacoustic Spectroscopy", Appl. Phys. Lett., 32 (9), May 1, 1978, p. 538 describes a preliminary study of photoacoustic microscopy using a gas-microphone detector system. Wickramasinghe et al "Photoacoustics on a Microscopic Scale", to be published in Appl. Phys. Lett., Dec. 1, 1978, describes the modification of a transmission acoustic microscope by replacing an input acoustic lens with an optical counterpart, a focused pulsed laser. The system operates at a very high fixed frequency of 840 MHz. Hordvik and Schlossberg, "Photoacoustic Technique for Determining Optical Absorption Coefficients in Solids", Applied Optics, Vol. 16, No. 1, January 1977, p. 101, describes a photoacoustic method using a contact transducer detector to measure the absorption coefficients of solids. White, J. Appl. Phys., 34, 3359 (1963) shows the generation of elastic waves by very high frequency surface heating. Callis, "The Calorimetric Detection of Excited States", J. Research N.B.S., Vol. 80A, No. 3, May-June 1976, p. 413 describes a piezoelectric calorimeter. Farrow et al, "Piezoelectric Detection of Photoacoustic Signals", Applied Optics, Vol. 17, No. 7, Apr. 1, 1978, p. 1093, describe the use of piezoelectric detectors instead of microphone detectors to measure optically generated acoustic signals in solids.

None of the prior art fully explores the physical mechanisms and potentials of photoacoustic microscopy. The prior art does not go to the underlying basis of operation, does not teach how to perform thermoacoustic microscopy with photoacoustics, and does not teach the many uses for photoacoustic microscopy.

There is a great need in many industries, particularly the semiconductor industry, to rapidly scan a bulk solid material on a microscopic scale to determine subsurface properties and to do so in a nondestructive manner. Information about subsurface structures, material changes, and competing energy-conversion properties is needed, and in particular the ability to obtain a depth-profile at various selected depths would be highly advantageous for quality control of devices early in the manufacturing process. Present optical techniques provide information about surface properties. Photoacoustic spectroscopy provides information as a function of wavelength as the source wavelength is varied, i.e. photoacoustically generated spectra, and only for the aggregate material, not on a microscopic scale.

It is an object of the invention to provide nondestructive measurements of surface and subsurface properties of a bulk solid on a microscopic scale.

It is also an object of the invention to provide nondestructive measurements of surface and subsurface features of a bulk solid on a microscopic scale through the interaction of photoacoustically generated thermal waves with the features.

It is another object of the invention to detect the presence of, and perform measurements on, fluorescent species, photochemical processes, and photovoltaic processes in a bulk solid on a microscopic scale.

It is a further object of the invention to provide a depth-profile of a bulk solid at various selected depths on a microscopic scale.

SUMMARY OF THE INVENTION

The invention is a method and apparatus for photoacoustic microscopy to scan a material as a two-dimensional array of microscopic, or more particularly thermoacoustic or thermal wave microscopy, spots, providing a variety of surface and subsurface information by the interaction of photoacoustically generated thermal waves with microscopic features of the material. A photoacoustic signal is generated at a microscopic spot in the material by focusing intensity modulated light onto the material. Alternatively, instead of visible light, radiation from any part of the electromagnetic spectrum, or any other heating source such as a particle beam could be used. The incident focused light is absorbed in a microscopic region of the material and causes localized heating, which produces a photoacoustic signal. The photoacoustic signal results from two deexcitation processes, the thermo-acoustic process which predominates at relatively low modulation frequencies, 1 Hz–20 MHz, and the elasto-acoustic process which predominates at high modulation frequencies usually greater than 10 MHz. Under most circumstances the most appropriate method for doing photoacoustic microscopy for most applications is at the relatively low frequencies where the thermo-acoustic process predominates. The preferred frequency range according to the invention is 10 KHz–20 MHz.

At frequencies where the thermoacoustic process is dominant, the localized heating produces thermal waves which travel a thermal diffusion length (a thermal wavelength) before they are effectively attenuated. These thermal waves also produce stress-strain or elastic waves that have a much longer wavelength and a much greater range. At frequencies where the elasto-acoustic process is dominant, the elastic waves have wavelengths that are comparable or even shorter than the thermal waves. At this point, energy from the region that is directly heated from the absorbed light or incident energy is more effectively converted directly into elastic waves rather than first into thermal waves and then into elastic waves.

The sample is scanned as a two-dimensional array of microscopic points by rastering the sample past the stationary focused beam of light, or alternatively by deflecting the beam across a fixed sample. The photoacoustic signal is detected by a piezoelectric transducer in contact with the sample, or coupled to the sample through a fluid. The piezoelectric transducer detects the acoustic waves produced by the thermal waves when operating in the thermoacoustic region. The signal is fed into a phase-sensitive lock-in amplifier tuned to the modulation frequency. The signal from the lock-in amplifier is then analyzed with an appropriate data processing system.

The photoacoustic microscope gives information on a microscopic scale of any surface or subsurface properties or structures which affect the absorption of the intensity-modulated light at the focused spot in the material. Surface and subsurface features of the sample are also detected through the interaction of photoacoustically generated thermal waves with these features. By sweeping the wavelength of the incident light, a microscopic absorption spectrum of the material can be obtained. The photoacoustic microscope provides information on a microscopic scale of the presence of competing modes of deexcitation, such as fluorescence, photochemistry, and photovoltaic processes, which alter the photoacoustic signal produced. Photoacoustic microscopy provides depth-profiling of the material on a microscopic scale. Scans of the material at various selected depths can be made. Depth-profiling can be done in three ways. The preferred method is to change the modulation frequency of the incident light, thereby changing the penetration depth of the thermal waves in the sample, and consequently the depth at which the photoacoustic signal is produced. This method will usually be performed in the low frequency range, 1 Hz–20 MHz. Depth-profiling can also be done by changing the wavelength of the incident light or analyzing the phase of the photoacoustic signal.

BRIEF DESCRIPTION OF THE DRAWINGS

Other objects and advantages of the invention will become apparent from the following detailed description, with reference to the accompanying drawings, in which.

DETAILED DESCRIPTION OF THE PREFERRED EMBODIMENT

The photoacoustic effect arises when intensity-modulated light, or other form of electromagnetic radiation or particle beam impinges on a sample. When localized heating occurs in a material, the heat energy is transmitted to the surrounding material through two mechanisms. First, there is a diffusion of heat from the originally heated area to the surrounding area via heat conduction and diffusion, i.e., a heat wave or thermal wave. The rate of energy transfer by this means is determined by the material's thermal diffusivity K. When the heating is periodic at a frequency $\omega$, then the distance of appreciable transfer of a periodic heat signal or thermal wave through the medium is given by the thermal wavelength or diffusion length $\mu_t = (2K/\omega)^{\frac{1}{2}}$. Energy transfer through thermal diffusion is a dissipative process, in which individual atoms, ions or molecules within the material are vibrationally excited in a non-cooperative manner. This mode of energy transfer is called the thermo-acoustic mode. The thermal wave in turn produces a pressure wave or acoustic wave in the sample which is a carrier of the information in the thermal wave.

The second mode of energy transfer is through the coupling of the local heat energy to the cooperative vibrational modes of the material itself, i.e., through a coupling to the sample's phonon spectrum. This is an elasto-acoustic process, which is generally non-dissipative. The speed of the energy transfer is governed by the speed of sound in the material, and the distance of appreciable energy transfer is limited solely by the dimensions of the sample or other boundary conditions, except at very high frequencies where ultrasonic attenuation can occur.

Figure 2:
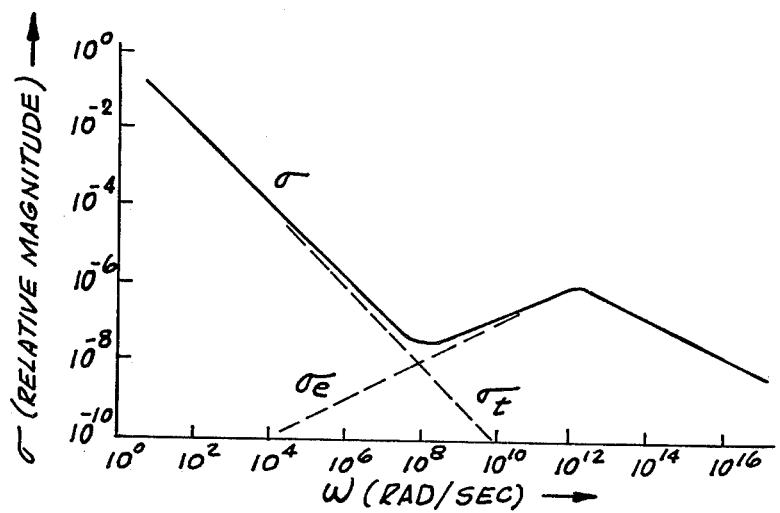
FIG. 2 is a diagram of the photoacoustic stress as a function of modulation frequency in the free surface case.
Figure 3:
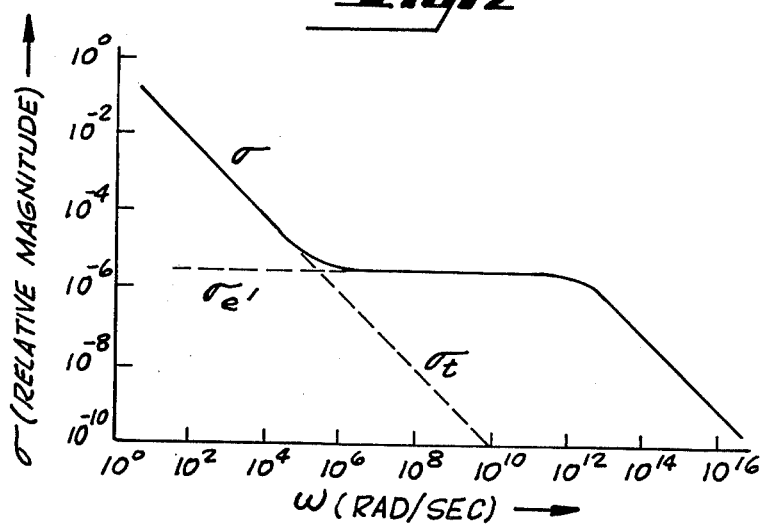
FIG. 3 is a diagram of the photoacoustic stress as a function of the modulation frequency in the constrained surface case.

Thus the photoacoustic signal arises from both thermo-acoustic and elasto-acoustic processes that are initiated by the absorption of intensity-modulated electromagnetic radiation. The photoacoustic stress produced in the material as a function of the modulation frequency of the incident light is shown in FIGS. 2 and 3 for the free surface and constrained surface cases, respectively. The total stress $\sigma$ is made up of the thermo-acoustic stress $\sigma_t$ and the elasto-acoustic stress $\sigma_e$. Because the stress or signal is strongest at the lower modulation frequencies, where the thermo-acoustic process dominates, this is the preferred region of operation in most cases. At high frequencies, the elasto-acoustic stress and signal can be increased by constraining the surface of the material at the point where it is heated.

Three physical processes are involved in photoacoustic microscopy, all of which can provide microscopic information about a material. The absorption of incident energy in a material results in the generation and propagation of thermal waves in the material, which in turn results in the generation and propagation of elastic or acoustic waves in the material. The invention utilizes photoacoustically generated thermal waves to provide microscopic information about a material.

The process of absorption of incident energy provides information about local absorption or reflection/scattering properties of a material, as in an optical microscope or an electron microscope. The ultimate resolution is determined by the photon or electron wavelength. The depth of visualization is determined by the penetration depth of photons, or the penetration or escape depths of electrons. For light the resolution is about one micron; for electrons, about 0.01 microns.

The process of generation and propagation of elastic or acoustic waves provides information about the local elastic properties of a material, as in conventional ultrasonic transmission techniques and the acoustic microscope. The ultimate resolution is determined by the wavelength of the acoustic waves; for most solid materials, the best resolution is 5–10 microns even at 1000 MHz. Higher resolutions are limited by the large acoustic attenuations at higher frequencies. Acoustic microscopy is generally performed in a transmission mode so depth profiling is not available.

The generation and propagation of thermal waves provides information about the local thermal properties of a sample. Visualization results from the interaction of thermal waves with features that have different thermal properties. This process is utilized only in the photoacoustic microscope as taught by the present invention, and not in optical or acoustic microscopes. The ultimate resolution is determined by the thermal wavelength, which is the thermal diffusion length. For most solids, the resolution is about one micron at 1–10 MHz. Thermal waves have high attenuation; the penetration depth is the thermal diffusion length, which is equal to the wavelength. Direct detection of thermal waves would therefore be limited to very thin samples. However, in photoacoustics the thermal waves are not detected directly, but indirectly through the stress-strain fluctuations or acoustic waves that are in turn produced by the thermal waves. The elastic waves, because of their much longer wavelengths, serve simply as carriers of the information that is derived from the interaction of the photoacoustically generated thermal waves with the sample. Only at very high frequencies where the acoustic wavelengths become short enough would the interaction of the elastic waves with the medium provide additional microscopic information about the sample. The photoacoustic or thermoacoustic microscope as taught by the invention is operated below 20 MHz to provide high resolution and to also provide long wavelength acoustic carrier waves.

Figure 1:
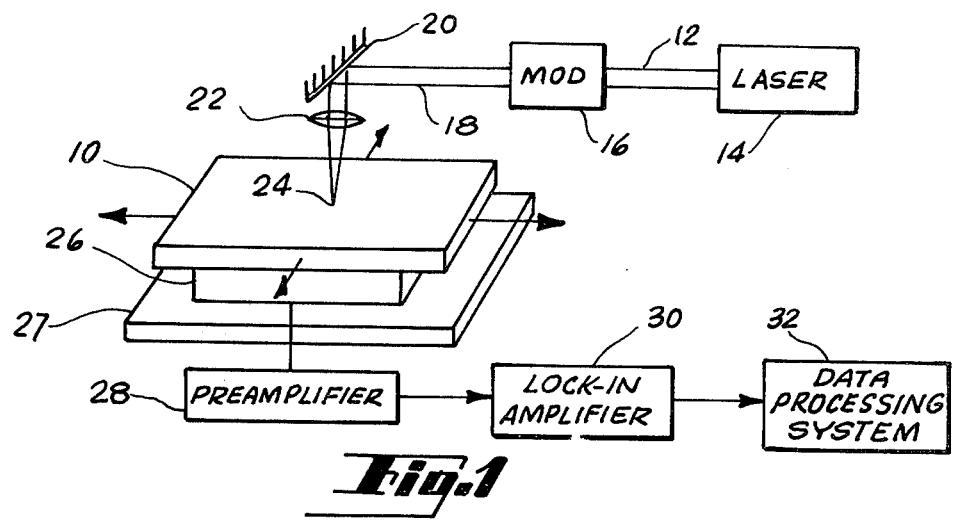
FIG. 1 is a schematic diagram of a system for performing photoacoustic miscroscopy of a bulk solid sample using the piezoelectric method.

A simple photoacoustic microscopy setup, as shown in FIG. 1, uses the piezoelectric method of photoacoustic detection to examine microscopic areas of a bulk solid sample 10, such as a silicon wafer. The preferred source is an optical beam 12, such as a laser beam from laser 14. The laser 14 is generally a cw laser. However, photoacoustic signals can be generated in the sample by the absorption of any other form of electromagnetic radiation other than visible light, e.g., radio frequency waves, microwaves, infrared light, ultraviolet light, X-rays, gamma rays, etc. In addition, photoacoustic signals can be generated through thermal excitations arising from the interaction with the sample of particle beams, such as beams of electrons, protons, neutrons, ions, atoms, or molecules.

The optical beam 12 is intensity-modulated by the intensity modulation system 16, such as an acousto-optic or electro-optic modulator. Alternatively, the optical beam can be wavelength-modulated in some cases to produce a photoacoustic signal. A particle beam would likewise be intensity modulated to cause periodic heating. The intensity modulated beam 18 is then deflected by mirror 20 and focused by a lens system 22 onto the sample. The incident optical radiation can readily be focused to a spot 24 as small as one micron on the sample so that a microscopic area of the sample is examined. A particle beam would likewise be focused to a spot that can often be much smaller than one micron. Since a bulk solid is being examined, the piezoelectric method of detection is best. The piezoelectric method is insensitive to airborne noise so no acoustically-sealed chamber is generally needed, and higher frequencies are possible, thereby permitting higher resolution. A piezoelectric crystal 26 is mounted in direct physical contact with the sample 10. Alternatively, the piezoelectric crystal could be coupled to the sample through a suitable fluid. The signal from the piezoelectric detector can be enhanced by operating at a resonance frequency of the detector or of the detector-sample system.

A complete microscopic scan of the sample is made by rastering the sample past the stationary focused optical beam by means of an electro-mechanical x-y rastering system 27. Alternatively, the sample could remain stationary and the beam could be deflected across the sample by a deflection mechanism such as an x-y opto-acoustic deflection system. In mass production applications, every point on the sample would not be examined but a number of points would be scanned on a statistical sampling basis.

Photoacoustic microscopy according to the invention is performed at the relatively low frequencies, below 20 MHz, where the thermo-acoustic process dominates rather than at very high frequencies where the elasto-acoustic process dominates. This is because a thermal wave resolution of one micron is possible in most materials for frequencies less than 10 MHz.

The photoacoustic signal produced at each point on the sample is detected by the piezoelectric transducer 26. The signal from the piezolelectric crystal is fed through a preamplifier 28 and then into a phase-sensitive lock-in amplifier 30 that is tuned to the modulation frequency. The signal from the lock-in amplifier is then fed into a suitable storage, processing, and display system 32. This system also controls the rastering system 27 or the beam deflection system.

Photoacoustic microscopy (PAM) is a very versatile method for scanning a bulk solid sample, such as a semiconductor wafer, revealing many different properties of the sample. PAM gives visual information on a microscopic scale. The light is focused to a microscopic spot size. The photoacoustic signal is directly related to the amount of light absorbed at the focused spot. Thus changes in the material or its geometric structure will change the absorption or reflection characteristics at the spot and thus alter the photoacoustic signal. A scan of the sample will give a picture similar to that obtained with a conventional optical microscope.

PAM gives optical absorption data on a microscopic scale. By changing the wavelength of the incident focused light beam, the optical absorption properties of the material can be measured. An optical absorption spectrum can thus be obtained on a microscopic scale.

PAM gives information about deexcitation processes on a microscopic scale. Since the photoacoustic signal arises from the deexcitation of the optical energy levels into localized heat, competing modes of deexcitation such as fluorescence, photochemistry, and photoelectricity, will affect the photoacoustic signal. The presence of fluorescent species, e.g., certain dopants or impurities, can be ascertained at each microscopic spot since the presence of fluorescence will diminish the photoacoustic signal. In addition, the fluorescent species can be identified by tuning the wavelength of the incident light through the absorption band or bands of the species. Photochemical processes can be detected by a change in the photoacoustic signal and identified by varying the incident wavelength. Similarly, the presence of a photovoltaic process will affect the photoacoustic signal. This has particular applicability to testing semiconductor devices. Certain defects in the device manufacture such as the presence of electrical shorts or leaks will alter the photoacoustic signal and thus be made apparent. This can be done in a nondestructive manner early in the manufacturing process. A detailed study of microscopic photovoltaic regions could be done by studying the time-dependence of the photoacoustic signal. This time-dependence can be determined by analyzing the phase of the photoacoustic signal detected by the piezoelectric transducer as a function of modulation frequency. Alternatively, the time-dependence can be determined by recording the time-evolution of the photoacoustic signal arising from a pulse of incident light. In the latter case, the cw laser and modulator would be replaced by a pulsed laser, and the lock-in amplifier would be replaced by a fast storage scope or a transient signal analyzer.

Of great significance, PAM provides for depth-profiling of the sample on a microscopic scale. Depth-profiling can be performed in three ways. First, by changing the wavelength of the incident light, the depth of optical penetration can be changed. Similarly, the energy of the incident particle beam can be changed. Second, by changing the frequency at which the light intensity or particle beam is modulated the depth from which the photoacoustic information is obtained is changed, through changes in the thermal wavelength. This results from the $\omega^{-\frac{1}{2}}$ dependence of the thermal diffusion length on the modulation frequency. For the case where the optical absorption length is short, e.g., less than $10^{-6}$ cm, the photoacoustic signal in a typical material can be made to originate from a depth as little as $0.1\mu$ at 100 MHz to as much as 0.1 cm at 1 Hz. Third, it is also possible in some cases to analyze the phase of the photoacoustic signal to determine whether the signal arose from the surface or below the surface.

An important application of the depth-profiling capability of the photoacoustic microscope, is the measurement of thin-film thicknesses on a microscopically localized scale. Such measurements can be performed by analyzing the magnitude and/or phase of the photoacoustic signal as a function of the modulation frequency. Alternatively, these measurements can be performed by analyzing the time-dependence of the photoacoustic signal generated by pulses of laser light or pulses from particle beams.

While the invention has been described in conjunction with specific embodiments thereof, many alternatives, modifications, and variations will be apparent to those skilled in the art in the light of the foregoing description. Accordingly, it is intended to embrace all such alternatives, modifications, and variations as fall within the spirit and broad scope of the appended claims.

I claim:

1. A method of thermoacoustic or thermal wave microscopy to examine surface and subsurface properties of a material on a microscopic scale, comprising:
   causing periodic localized heating at a microscopic spot in the material, to produce thermal waves which interact with microscopic features in the material to provide thermal wave imaging of the features, the thermal waves producing acoustic waves of longer wavelength in the material which propagate through the material;
   detecting the acoustic waves produced in the material, producing detector signals;
   scanning the material as a two-dimensional array of microscopic spots; and
   processing the detector signals.

2. The method of claim 1 wherein the source of heating is electromagnetic radiation.

3. The method of claim 2 wherein the electromagnetic radiation is light.

4. The method of claim 3 for depth-profiling the material by taking successive scans of the material at various selected depths, further comprising the step of changing the wavelength of the light to various selected wavelengths.

5. The method of claim 3 for detecting the presence of fluorescent species, photochemical processes, and photovoltaic processes, further comprising the step of detecting a change in the detector signal.

6. The method of claim 5 for identifying the fluorescent species, further comprising the step of varying the wavelength of the light source.

7. The method of claim 5 for identifying the localized occurrence of photochemical and photovoltaic processes, further comprising the step of varying the wavelength of the light source.

8. The method of claim 7 wherein the time-dependence is determined by measuring the detector signal arising from a pulse of incident light as a function of time.

9. The method of claim 2 wherein the periodic heating is performed by wavelength modulation of the electromagnetic radiation.

10. The method of claim 1 wherein the source of heating is a particle beam.

11. The method of claim 4 for depth-profiling the material by taking successive scans of the material at various selected depths, further comprising the step of changing the energy of the particle beam to various selected energies.

12. The method of claim 1 wherein the localization of the heating at a microscopic spot in the material is performed by a focusing mechanism.

13. The method of claim 1 wherein the periodic heating of the material is performed by intensity modulation of the heating source.

14. The method of claim 13 for depth-profiling the material by taking successive scans of the material at various selected depths, further comprising the step of selectively changing the modulation frequency on successive scans.

15. The method of claim 13 for studying the localized occurrence of photochemical and/or photovoltaic processes, further comprising the step of analyzing the time-dependence of the detector signal by measuring the magnitude and/or phase of the detector signal as a function of the modulation frequency.

16. The method of claim 13 for measuring the thickness of thin films, further comprising the step of analyzing the magnitude and/or phase of the detector signal as a function of the modulation frequency.

17. The method of claim 13 wherein the intensity modulation is at a frequency below 20 MHz.

18. The method of claim 1 wherein the photoacoustic signal is detected by a piezoelectric device.

19. The method of claim 18 wherein the signal from the piezoelectric device is enhanced by operating at a resonance frequency of the piezoelectric detector or of the detector-material system.

20. The method of claim 1 for depth-profiling the material, further including the step of analyzing the phase of the detector signal.

21. The method of claim 1 for detecting the presence of fluorescent species, photochemical processes, and photovoltaic processes on a microscopic scale, further comprising the step of detecting a change in the detector signal produced from each microscopic spot in the material.

22. The method of claim 21 for studying the localized occurrence of photochemical and photovoltaic processes, further comprising the step of detecting the time-dependence of the detector signal.

23. The method of claim 1 for measuring the thickness of thin films, further comprising the step of analyzing the time-dependence of the detector signal generated by a pulsed heating source.

24. The method of claim 1 wherein the periodic localized heating is at a frequency below 20 MHz.

25. A thermoacoustic or thermal wave microscope for measuring surface and subsurface properties of a material on a microscopic scale, comprising:

heating means for causing periodic localized heating at a microscopic spot in the material, to produce thermal waves which interact with microscopic features in the material to provide thermal wave imaging of the features, the thermal waves producing acoustic waves of longer wavelength in the material which propagate through the material;

detection means for detecting the acoustic waves produced in the material, producing detector signals;

scanning means for scanning the material as a two-dimensional array of microscopic spots; and processing means for processing the detector signals.

26. The apparatus of claim 25 wherein the heating means is a source of electromagnetic radiation.

27. The apparatus of claim 26 wherein the source of electromagnetic radiation is a cw laser.

28. The apparatus of claim 26 wherein the periodic heating of the material is performed by wavelength modulation of the source of electromagnetic radiation.

29. The apparatus of claim 25 wherein the heating means is a particle beam.

30. The apparatus of claim 25 wherein the localization of the heating at a microscopic spot in the material is performed by a focusing mechanism.

31. The apparatus of claim 25 wherein the periodic heating of the material is performed by intensity modulation of the heating means.

32. The apparatus of claim 31 wherein the intensity modulation is at a frequency below 20 MHz.

33. The apparatus of claim 25 wherein the detection means is a piezoelectric device.

34. The apparatus of claim 25 wherein the heating means produces periodic localized heating at a frequency below 20 MHz.

* * * * *